United States Patent [19]

Watts

[11] 4,107,317

[45] * Aug. 15, 1978

[54] CHROMAN DERIVATIVES

[75] Inventor: Eric Alfred Watts, Harlow, England

[73] Assignee: Beecham Group Limited, United Kingdom

[*] Notice: The portion of the term of this patent subsequent to Sep. 13, 1994, has been disclaimed.

[21] Appl. No.: 786,139

[22] Filed: Apr. 11, 1977

Related U.S. Application Data

[62] Division of Ser. No. 577,614, May 14, 1975, Pat. No. 4,048,317.

[30] Foreign Application Priority Data

May 31, 1974 [GB] United Kingdom ............... 24348/74

[51] Int. Cl.$^2$ .................. A61K 31/445; C07D 405/04

[52] U.S. Cl. .................. 424/267; 424/274; 424/283; 544/142; 544/150; 544/151; 544/185; 260/293.58; 260/296 B; 260/326.34; 260/326.5 CA; 260/345.2; 260/512 C; 544/376; 544/378; 544/372

[58] Field of Search .................. 260/296 B; 424/267, 424/274, 283

[56] References Cited

U.S. PATENT DOCUMENTS 4,048,317  9/1977  Watts .................................. 424/267

Primary Examiner—John D. Randolph
Attorney, Agent, or Firm—Jacobs & Jacobs

[57] ABSTRACT

Derivatives of trans-3-hydroxy-4-amino-chroman and pharmaceutical compositions containing such derivatives are useful for effecting vasodilation in mammals, including humans.

28 Claims, No Drawings

CHROMAN DERIVATIVES

CROSS-REFERENCE

This is a division of Ser. No. 577,614 filed May 14, 1975, now U.S. Pat. No. 4,048,317.

The present invention relates to chroman derivatives, to a process for their preparation and to pharmaceutical compositions containing them.

More specifically, this invention relates to derivatives of trans-3-hydroxy-4-amino-chroman which possess blood pressure lowering activity, to their preparation by the reaction of amines on chroman epoxide derivatives and to pharmaceutical compositions containing the compounds of the invention which may be used in the treatment of hypertension in mammals including humans.

The compounds according to this invention are of the formula (I):

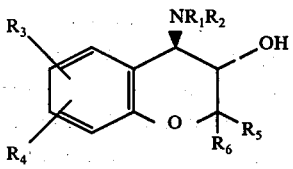

and acid addition salts thereof wherein $R_1$ is a hydrogen atom or a $C_{1-9}$ hydrocarbon group optionally substituted by a hydroxyl or $C_{1-6}$ alkoxyl group; $R_2$ is a hydrogen atom or $C_{1-6}$ alkyl group, or $NR_1R_2$ is a 3-8 membered heterocyclic group optionally substituted by one or two methyl groups; $R_3$ is a hydrogen or halogen atom or a $C_{1-6}$ alkyl, $C_{2-6}$ alkenyl, $C_{1-6}$ alkoxyl, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_7$, $ASR_7$, $ASO_2R_7$, $ANHR_7$, $ANR_7COR_8$, $ANR_7SO_2R_8$ or $ANR_7CO_2R_8$ group wherein A is an alkylene group of 1-4 carbon atoms, $R_7$ is an alkyl group of 1-4 carbon atoms and $R_8$ is an alkyl group of 1-4 carbon atoms; $R_4$ is a hydrogen or halogen atom or methyl or methoxy, or $R_3$ together with $R_4$ forms a $-CH=CH-CH=CH-$, $-NH-CH=CH-$, $-CH_2-CH_2-CH_2-CH_2-$ or $-CH_2-CH_2-CH_2-CO-$ system; $R_5$ is a hydrogen atom or a $C_{1-6}$ alkyl or phenyl group; and $R_6$ is a hydrogen atom or a $C_{1-6}$ alkyl or phenyl group.

Suitable groups $R_1$ include the hydrogen atom and the methyl, ethyl, n-propyl, iso-propyl, n-butyl, iso-butyl, sec-butyl, t-butyl, n-pentyl, iso-pentyl, hexyl, allyl, phenyl, benzyl, tolyl, cyclopropylmethyl, cyclohexyl and the like groups.

Particularly suitable groups $R_1$ include $C_{1-6}$ alkyl groups.

Suitable groups $R_2$ include the hydrogen atom and the methyl, ethyl, propyl and like groups.

Suitable heterocyclic groups $NR_1R_2$ include the pyrrolidyl, piperidyl, morpholino, methylpyrrolidyl, N-methylpiperazine, hexamethyleneamino, N-phenylpiperazine, hexamethylenetetramine and the like groups.

Especially suitable groups $R_5$ and $R_6$ include the methyl and ethyl groups.

Preferred groups $R_5$ and $R_6$ include the methyl group.

Particularly suitable compounds of the formula (I) wherein $R_4$ is a hydrogen atom include those of the formula (II):

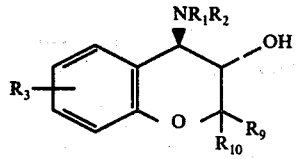

and their salts wherein $R_3$ is as defined in relation to formula (I), $R_9$ is a methyl or ethyl group, $R_{10}$ is a methyl or ethyl group and either (a), $NR_1R_2$ is a group $NR_{11}R_{12}$ wherein $R_{11}$ is an alkyl group of 1-4 carbon atoms and $R_{12}$ is a hydrogen atom or a methyl or ethyl group or (b) $NR_1R_2$ is a group of the sub-formula:

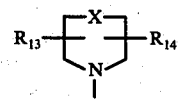

wherein X is a bond joining the two carbon atoms or is a $CH_2$, $CH_2.CH_2$, $CH_2.CH_2.CH_2$, $CH:CH$, O, S or $NCH_3$ group, $R_{13}$ is a hydrogen atom or a methyl group and $R_{14}$ is a hydrogen atom or a methyl group.

Most suitably, $NR_{11}R_{12}$ is a $N(CH_3)_2$ or NH $C_{1-4}$ alkyl group.

Most suitably X is a bond or a $CH_2$ or $CH_2CH_2$ group.

Particularly suitable groups $R_3$ for inclusion in compounds of the formula (I) or (II) include the allyl, allyloxy, nitro, trifluoromethyl, nitrile, $NH.CO.R_{16}$, $NHSO_2R_{16}$, $NHSO_3R_{16}$, $(CH_2)_nOR_{16}$ or $(CH_2)_nNH.CO.R_{16}$ where $R_{16}$ is an alkyl group of 1-4 carbon atoms and $n$ is 1, 2 or 3.

A further particularly suitable group of compounds of the formula (I) is that of the formula (III):

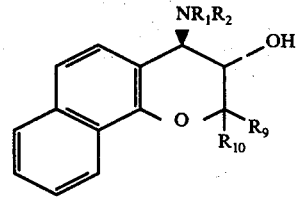

and salts thereof wherein $NR_1R_2$, $R_9$ and $R_{10}$ are as defined in relation to formula (II).

Particularly suitable groups $NR_1R_2$ in compounds of formulae (I), (II) or (III) include $NHC(CH_3)_3$, $NH.CH(CH_3)_2$, pyrrolidyl and piperidyl groups.

Particularly suitable groups $R_5$, $R_6$, $R_9$ and $R_{10}$ for inclusion in compounds of formulae (I), (II) or (III) include the methyl group.

One suitable sub-group of the compounds of formula (I) are those of formula (IV):

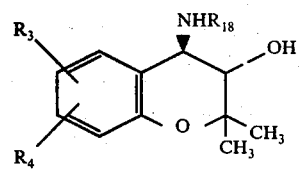

and salts thereof wherein $R_{18}$ is a $C_{1-6}$ alkyl, phenyl or benzyl group and $R_3$ and $R_4$ are as defined in relation to formula (I).

Most suitably $R_{18}$ is an iso-propyl, iso-butyl or t-butyl group.

A further sub-group of the compounds of formula (I) worthy of mention are those of formula (V):

$$\text{(V)}$$

[Structure: benzene ring with $R_3$ and $R_4$ substituents, bearing a side chain $-CH(NHCH(CH_3)_2)-CH(OH)-$ connected via O to $C(CH_3)_2$]

and salts thereof wherein $R_3$ and $R_4$ are as defined in relation to formula (I).

Suitable groups $R_3$ for inclusion in the compounds of formulae (II), (IV) or (V) include the hydrogen, fluorine, chlorine and bromine atoms and the methyl, ethyl, propyl, allyl, trifluoromethyl, methoxyl, methylthio, hydroxyl, nitro, allyloxyl, amino, acetamido, methoxysulphonylamino and the like groups.

Suitable groups $R_4$ for inclusion in the compounds of formulae (I), (IV) or (V) include the hydrogen, fluorine and chlorine atoms and the methyl and methoxyl groups.

Particularly suitable groups $R_3$ for inclusion in the compounds of the formula (II), (IV) or (V) include the hydrogen, fluorine and chlorine atoms and the methyl, trifluoromethyl, allyl, nitro, amino, acetamido, allyloxyl and methoxysulphonylamino groups.

Particularly suitable groups $R_4$ for inclusion in the compounds of the formulae (I), (IV) or (V) include the hydrogen and chlorine atoms, the hydrogen atom being preferred.

Further suitable values for $R_3$ for inclusion in the compounds of the formulae (II), (IV) or (V) are $(CH_2)_nOR_{19}$, $(CH_2)_nSR_{19}$, $(CH_2)_nSO_2R_{19}$, $(CH_2)_nNHCOR_{19}$, $(CH_2)_nNHCO_2R_{19}$ and $(CH_2)_nN(CH_3)COR_{19}$ groups wherein $n$ is 1, 2 or 3 and $R_{19}$ is a methyl or ethyl group.

Compounds having vasodilatory activity may be found within formula (VI):

$$\text{(VI)}$$

[Structure: benzene ring with $O_2N-$ substituent, bearing a side chain $-CH(NR_1R_2)-CH(OH)-$ connected via O to $CR_5R_6$]

and salts thereof wherein $R_1$, $R_2$, $R_5$ and $R_6$ are as defined in relation to formula (I).

Most suitably, $NR_1R_2$ is a cyclic group of sub-formula (b) as defined in relation to formula (II).

Most suitably, $R_5$ is a methyl or ethyl group and $R_6$ is a methyl or ethyl group.

Preferably $R_5$ and $R_6$ are both methyl groups.

Acid addition salts of the amino compounds of formulae (I) - (VI) may be made with acids in conventional manner. Suitable salt-forming acids include hydrochloric, hydrobromic, sulphuric, phosphoric, methanesulphonic, p-toluenesulphonic, acetic, propionic, succinic, citric, tartaric, mandelic, lactic, gluconic or other pharmaceutically acceptable organic or inorganic acid.

The compounds of the invention exist in optically active forms. Those skilled in the chemical arts will realise that racemic mixtures of amino compounds can often be separated into pure optical isomers using such techniques as fractional crystallisation with optically active acids and the like.

The compounds of formula (I) may be prepared by the reaction of an amine of the formula $NHR_1R_2$ with an epoxide of the formula (VII):

$$\text{(VII)}$$

[Structure: benzene ring with $R_3$ and $R_4$ substituents, bearing an epoxide side chain connected via O to $CR_5R_6$]

wherein $R_3$, $R_4$, $R_5$ and $R_6$ are as defined in relation to formula (I).

The reaction of the amine and epoxide may be carried out at any non-extreme low, medium or high temperature (for example, $-10°$ C to $200°$ C) but in general ambient or slightly elevated temperatures are most suitable (for example, $12°$ C to $100°$ C). The reaction is normally carried out in the presence of a solvent such as alkanolic or ketonic solvent (for example, methanol, ethanol, propanol, acetone or methylethylketone).

It has been found that the reaction frequently proceeds smoothly and efficiently if the reaction is carried out in warmed or refluxing ethanol.

The above reaction has been found to give a trans product substantially free from the cis-isomer.

Compounds of formula (I) wherein $R_3$ is an amino group or substituted amino group may also be prepared by reduction (and optionally thereafter acylation or sulphonation) of the corresponding compound in which $R_3$ is a nitro group. Similarly, hydroxyl groups may be alkylated by conventional methods under conventional conditions if desired.

Frequently, pure compounds of this invention prepared by the preceding method may form crystals which contain water of crystallisation, for example, from 1 to 4 molecules of water per compound of formula (I).

The useful intermediates of the formula (VII) may be prepared by the method of Livingstone, R.; (J. Chem. Soc., 76 (1962)).

This method is summarised by reaction sequence A.

[Reaction sequence A:

Benzene ring with $R_3$, $R_4$ substituents and $-OH$ + $Cl \cdot CR_6R_6 \cdot C\equiv CH$ $\downarrow K_2CO_3$/ Acetone/Heat Benzene ring with $R_3$, $R_4$ substituents, $-O-CR_5R_6-C\equiv CH$ $\downarrow$ Heat In Diethylaniline]

-continued

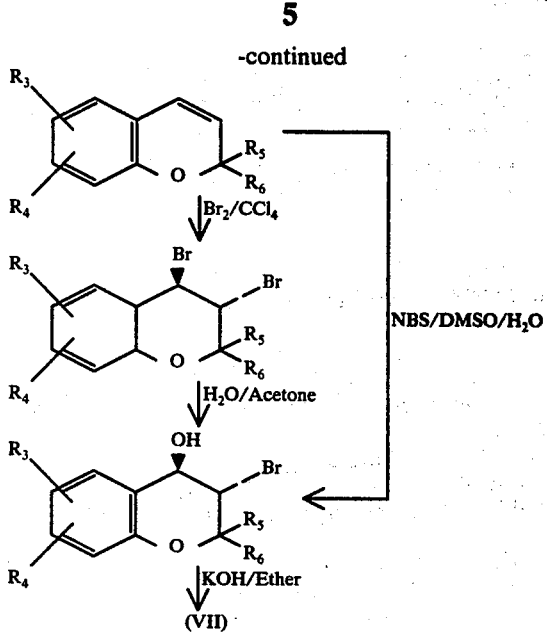

What we claim is:

1. A pharmaceutical composition useful for effecting vasodilation in humans and animals which comprises a vasodilatory amount of a compound of the formula

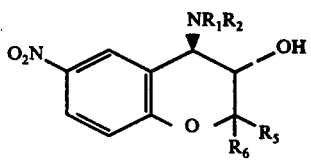

or a pharmaceutically acceptable acid addition salt thereof wherein $NR_1R_2$ is a 3- to 8-membered heterocycle wherein the nitrogen atom is the only heteroatom, unsubstituted or substituted by 1 or 2 methyl groups;

$R^5$ is hydrogen, alkyl of 1 to 6 carbon atoms or phenyl; and $R^6$ is hydrogen, alkyl of 1 to 6 carbon atoms or phenyl, in combination with a pharmaceutically acceptable carrier.

2. A composition according to claim 1 wherein $NR_1R_2$ is a moiety of the formula

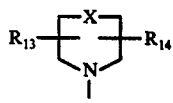

wherein X is a bond joining the two carbon atoms, $CH_2$, $CH_2$—$CH_2$, $CH_2$—$CH_2$—$CH_2$, or $CH$=$CH$;

$R_{13}$ is hydrogen or methyl; and $R_{14}$ is hydrogen or methyl.

3. A composition according to claim 1 wherein $NR_1R_2$ is a pyrrolidyl, piperidyl, methylpyrrolidyl or hexamethyleneimino moiety.

4. A composition according to claim 2 wherein $R_5$ and $R_6$ are each methyl or ethyl.

5. A composition according to claim 2 wherein $R_5$ and $R_6$ are each methyl.

6. A composition according to claim 3 wherein X is a bond joining the two carbon atoms, $CH_2$ or $CH_2$—$CH_2$.

7. A composition according to claim 1 wherein the compound is in the form of an acid addition salt wherein said salt is selected from the group consisting of the hydrochloride, hydrobromide, sulphate, phosphate, methane sulfonate, p-toluene sulfonate, acetate, propionate, succinate, citrate, tartrate, mandelate, lactate and gluconate.

8. A composition according to claim 1 wherein the compound is trans 4-piperidino-3,4-dihydro-2,2-dimethyl-6-nitro-2H-benzo[b]pyran-3-ol hydrochloride.

9. A composition according to claim 1 wherein the compound is trans-4-pyrrolidino-3,4-dihydro-2,2-dimethyl-6-nitro-2H-benzo[b]pyran-3-ol hydrochloride.

10. A composition according to claim 1 wherein the compound is trans-4-[4-methylpiperidino]-3,4-dihydro-2,2-dimethyl-6-nitro-2H-benzo[b]pyran-3-ol hydrochloride.

11. A composition according to claim 1 wherein the compound is trans-4-hexamethylenimino-3,4-dihydro-2,2-dimethyl-6-nitro-2H-benzo[b]pyran-3-ol hydrochloride.

12. A composition according to claim 1 wherein the compound is trans-4-heptamethylenimino-3,4-dihydro-2,2-dimethyl-6-nitro-2H-benzo[b]pyran-3-ol hydrochloride.

13. A composition according to claim 1 wherein the compound is trans-4-[2,4-dimethylpyrrolidino]-3,4-dihydro-2,2-dimethyl-6-nitro-2H-benzo[b]pyran-3-ol hydrochloride.

14. A composition according to claim 1 wherein the compound is trans-4-pyrrolidino-3,4-dihydro-2,2-diethyl-2H-benzo[b]pyran-3-ol hydrochloride.

15. A method of effecting vasodilation in humans and animals which comprises administering to a human or animal in need thereof a vasodilatory amount of a compound of the formula

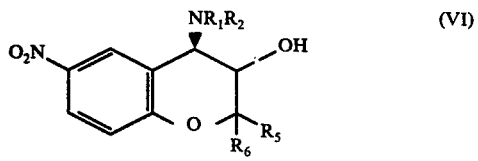

or a pharmaceutically acceptable acid addition salt thereof wherein $NR_1R_2$ is a 3- to 8-membered heterocycle wherein the nitrogen atom is the only heteroatom, unsubstituted or substituted by 1 or 2 methyl groups;

$R_5$ is hydrogen, alkyl of 1 to 6 carbon atoms or phenyl; and $R_6$ hydrogen, alkyl of 1 to 6 carbon atoms or phenyl, in combination with a pharmaceutically acceptable carrier.

16. A method according to claim 15 wherein $NR_1R_2$ is a moiety of the formula

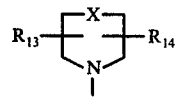

wherein X is a bond joining the two carbon atoms, $CH_2$, $CH_2$—$CH_2$, $CH_2$—$CH_2$—$CH_2$, or $CH$=$CH$;

$R_{13}$ is hydrogen or methyl; and $R_{14}$ is hydrogen or methyl.

17. A method according to claim 15 wherein $NR_1R_2$ is pyrrolidyl, piperidyl, methylpyrrolidyl or hexamethyleneimino moiety.

18. A method according to claim 15 wherein $R_5$ and $R_6$ are each methyl or ethyl.

19. A method according to claim 15 wherein $R_5$ and $R_6$ are each methyl.

20. A method according to claim 15 wherein X is a bond joining the two carbon atoms, $CH_2$ or $CH_2$—$CH_2$.

21. A method according to claim 15 wherein the compound is in the form of an acid addition salt wherein said salt is selected from the group consisting of the hydrochloride, hydrobromide, sulphate, phosphate, methane sulfonate, p-toluene sulfonate, acetate, propionate, succinate, citrate, tartrate, mandelate, lactate and gluconate.

22. A method according to claim 15 wherein the compound is trans-4-piperidino-3,4-dihydro-2,2-dimethyl-6-nitro-2H-benzo[b]pyran-3-ol hydrochloride.

23. A method according to claim 15 wherein the compound is trans-4-pyrrolidino-3,4-dihydro-2,2-dimethyl-6-nitro-2H-benzo[b]pyran-3-ol hydrochloride.

24. A method according to claim 15 wherein the compound is trans-4-[4-methylpiperidino]-3,4-dihydro-2,2-dimethyl-6-nitro-2H-benzo[b]pyran-3-ol hydrochloride.

25. A method according to claim 15 wherein the compound is trans-4-hexamethylenimino-3,4-dihydro-2,2-dimethyl-6-nitro-2H-benzo[b]pyran-3-ol hydrochloride.

26. A method according to claim 15 wherein the compound is trans-4-heptamethylenimino-3,4-dihydro-2,2-dimethyl-6-nitro-2H-benzo[b]pyran-3-ol hydrochloride.

27. A method according to claim 15 wherein the compound is trans-4-[2,4-dimethylpyrrolidino]-3,4-dihydro-2,2-dimethyl-6-nitro-2H-benzo[b]pyran-3-ol hydrochloride.

28. A method according to claim 15 wherein the compound is trans-4-pyrrolidino-3,4-dihydro-2,2-diethyl-2H-benzo[b]pyran-3-ol hydrochloride.

* * * * *